United States Patent
Cohen et al.

[19]

[11] Patent Number: 5,955,886
[45] Date of Patent: Sep. 21, 1999

[54] MICROLITER-SIZED IONIZATION DEVICE AND METHOD

[75] Inventors: Martin J. Cohen, West Palm Beach; Robert M. Simac, Palm Beach Gardens; Roger F. Wernlund, Lake Worth, all of Fla.

[73] Assignee: PCP, Inc., West Palm Beach, Fla.

[21] Appl. No.: 08/890,946

[22] Filed: Jul. 10, 1997

[51] Int. Cl.[6] .................................................. G01N 27/62
[52] U.S. Cl. .......................... 324/464; 324/71.1; 250/324; 250/423 R; 313/231.71; 73/23.4
[58] Field of Search ..................................... 324/459, 464, 324/465, 469, 470, 71.1; 73/23.35, 23.4, 23.42, 31.05, 861.09, 28.04; 250/382, 324, 384, 389, 374, 379, 385.1, 385.2, 426, 427, 423 R, 423 F; 313/231.41, 231.71; 315/111.01, 111.81, 111.91; 436/153

[56] References Cited

U.S. PATENT DOCUMENTS

| | | | |
|---|---|---|---|
| 3,566,107 | 2/1971 | Taylor et al. | 250/385.1 |
| 4,804,486 | 2/1989 | Hall | 250/432 R |
| 4,873,862 | 10/1989 | Scott et al. | 73/23.4 |
| 4,975,648 | 12/1990 | Lawson et al. | 324/464 |
| 5,739,699 | 4/1998 | Abdel-Rahman | 324/465 |
| 5,847,494 | 12/1998 | Bayliss et al. | 313/231.71 |

*Primary Examiner*—Diep Do
*Attorney, Agent, or Firm*—Schweitzer Cornman Gross & Bondell LLP

[57] ABSTRACT

A microliter-sized metastable ionization device with a cavity, a sample gas inlet, a corona gas inlet and a gas outlet. A first electrode has a hollow and disposed in the cavity and is in fluid communication with the sample gas inlet. A second electrode is in fluid communication with the corona gas inlet and is disposed around the first electrode adjacent the hollow end thereof. A gap forming means forms a corona gap between the first and second electrodes. A first power supply is connected to the first electrode and the second power supply is connected to the second electrode for generating a corona discharge across the corona gap. A collector has a hollow end portion disposed in the cavity which is in fluid communications with the gas outlet for the outgassing and detection of ionized gases. The first electrode can be a tubular member aligned concentrically with a cylindrical second electrode. The gap forming means can be in annular disc projecting radially inwardly from the cylindrical second electrode. The collector can have a tubular opening aligned coaxially with the first electrode and has an end face spaced a short distance from an end face of the first electrode forming a small active volume therebetween for the generation and detection of small quantities of trace analytes.

33 Claims, 8 Drawing Sheets

MICROLITER-SIZED IONIZATION DEVICE AND METHOD

This invention was made with Government support under contract number NAS2-14364 awarded by NASA. The Government has certain rights in the invention.

FIELD OF THE INVENTION

This invention relates to the field of detection and identification of trace amounts of gases and, in particular, to metastable ionization detectors.

BACKGROUND AND SUMMARY OF THE INVENTION

There is an increased commercial need for the measurement of gases that are present in trace amounts, typically in concentrations of 100 parts-per-billion and less. Ion mobility spectrometry (IMS, previously known as plasma chromatography) is one particularly useful technique for the determination of analyte gases in trace amounts. Another particularly useful technique for detecting trace amounts of gases is metastable ionization detection (MID).

In IMS devices, such as that described in U.S. Pat. No. 5,457,316, the trace chemicals to be detected are ionized and then separated from each other due to their differing drift velocities in an electric field. The time differentials of their arrivals to a collector are then registered. Hence the name "ion mobility".

In metastable ionization detection (MID), a gas sample mixture is directed through a separator, such as a gas chromatograph column, wherein the trace gas(es) are delayed by varying time periods. The time-delayed gases are then introduced sequentially into a chamber wherein metastable atoms of a rare gas (such as helium, argon, neon, etc.) are generated which interact with and ionize the trace gases. The ionized trace gases are then detected by a collector and are positively identified by the amount of time delay.

While the IMS and the MID (with a gas chromatograph) devices can effectively identify trace amounts of certain gases, they typically require a radiation source, such as a nickel-63 beta-radiation source for ionization. Such an ionization source is impractical for some commercial and aerospace applications. Also, prior IMS and MID designs can require more supplies and power than is available for such applications.

Since the MID was first described in 1958 by J. E. Lovelock, many investigators have experimented with different electrode and housing configurations. One such configuration, which has a reported cavity volume of 80 microliters and is a current candidate for a space-qualified MID, is the miniature triaxial MID described in The Triaxial Metastable Ionization Detector, Anal. Chem. 56, 860–862, F. H. Woeller, D. K. Kojiro and G. C. Carle (1984). Work with this and other prior designs has shown that a reduction in detector volume often correlates to an increase in sensitivity, depending on certain factors such as the mechanism of detection, the quantity of gas available to analyze, and the noise or instability characteristic of the device.

The drive to develop ever smaller and more sensitive detectors is fueled by the availability of miniaturized gas chromatographs, as well as weight considerations and the limited availability of consumable gas supplies and other utilities in certain applications (such as space exploration). An innovation of this invention is the use of a novel structure for a Micro-Volume Metastable Ionization Detector (MVID) which achieves a goal of an active volume (not cavity volume) of less than one microliter ($10^{-3}$ ml). The MVID is also adaptable to microbore and microchannel gas chromatographs, and because of the small internal volume of this detector, low gas flows (in the range of 1 ml/min) are permitted.

Generally, prior art MIDs have two functions—the generation of metastable atoms and the detection of the sample ions caused by the interaction of the neutral metastable atoms with the sample gases. The ions produced from interaction with metastable atoms generate a signal when detected by the collector, such as an electrometer. A detailed description of the initial ion generation processes in the type of electrode structure in the MVID can be found in J. D. Cobine, *Gaseous Conductors*, (Dover Publications: NY 1958), p 258, the disclosure of which is herein incorporated by reference.

In conventional metastable ionization detectors, there is usually only one electrical circuit. This one circuit measures the sum of all ion processes including both the radiation ionization (e.g. from tritium or nickel-63) and the ion multiplication from the electron flow across the gap. In addition, the detection current is mixed in with this current and, since the threshold is only about 1/100th of the standing current, a large part of the electrometer current must be subtracted in order to measure the signal current.

In the MVID, the two functions of generation and detection are decoupled. Therefore the currents and voltages, and even the gap spacings, can be different. Thus the two functions can be optimized independently of one another.

Specifically, one embodiment of an MVID made in accordance with the present invention comprises an insulating body with a small (40–60 microliter cavity volume) center core into which three electrode tubes extend. An outer electrode tube is disposed around and aligned concentrically with an inner electrode tube. A collector electrode, such as an electrometer electrode tube, is aligned coaxially with the inner electrode tube in an end-to-end fashion within the center core such that the collector electrode tube has an end face spaced a short distance from an end face of the inner electrode tube within the center core. The two end faces partially define a small active volume (1 microliter) of the center core. The inner electrode tube is connected to a sample gas inlet and the outer electrode tube is connected to a corona gas inlet. The collector electrode is connected to a gas outlet. A disc extends radially inwardly from the outer electrode tube forming a narrow annular corona gap between the disc and the inner electrode. Separate power supplies are connected to the inner and outer electrodes to create a corona discharge across the annular corona gap. A collector, such as an electrometer, and read out instruments are connected to the collector electrode to detect ions generated in the MVID as they exit through the electrometer tube.

In the operation of the MVID, a mixture of sample analyte gas(es) and a carrier gas is introduced into the center core through the inner electrode. A corona gas, which is a substantially pure form of the carrier gas, is introduced into the center core through the outer electrode tube. As the corona gas passes through the corona gap, metastable forms of the corona gas are created which flow into the center core in a concentric manner with the sample gas. In the small active volume between the inner electrode and the collector electrode, the metastable species interact with and ionize the analyte sample gas(es). The analyte ions formed are then detected as the gas mixture exits the MVID through the coaxially-aligned collector electrode.

The MVID of the present invention has an active volume of under 1 microliter and a cavity volume of only 40–60 microliters. In addition, the dimensions and spacing of the electrode tubes are in the millimeter range. These small volumes allow the MVID to accommodate low gas flows of about 1 ml/min thereby resulting in low consumption of gas samples. Also, since the MVID uses an electronic corona discharge to ionize the gas samples, no radiation source is required. In addition, the signal current and ion generation current in the MVID are separate, therefore they can be adjusted and optimized separately. These features provide detection for some organic gases in extremely low quantities and concentrations and in a manner which is compatible with many applications. Specifically, the potential applications for the MVID include analysis of planetary and cometary atmospheres, environmental monitoring, detection of drug, explosive and chemical agents, and as a novel ionization source for the above described ion mobility spectrometry processes.

BRIEF DESCRIPTION OF THE DRAWINGS

For a complete understanding of the above and other features of the invention, reference shall be made to the following detailed description of the preferred embodiments of the invention and to the accompanying drawings, wherein.

DETAILED DESCRIPTION OF THE INVENTION

Figure 1:
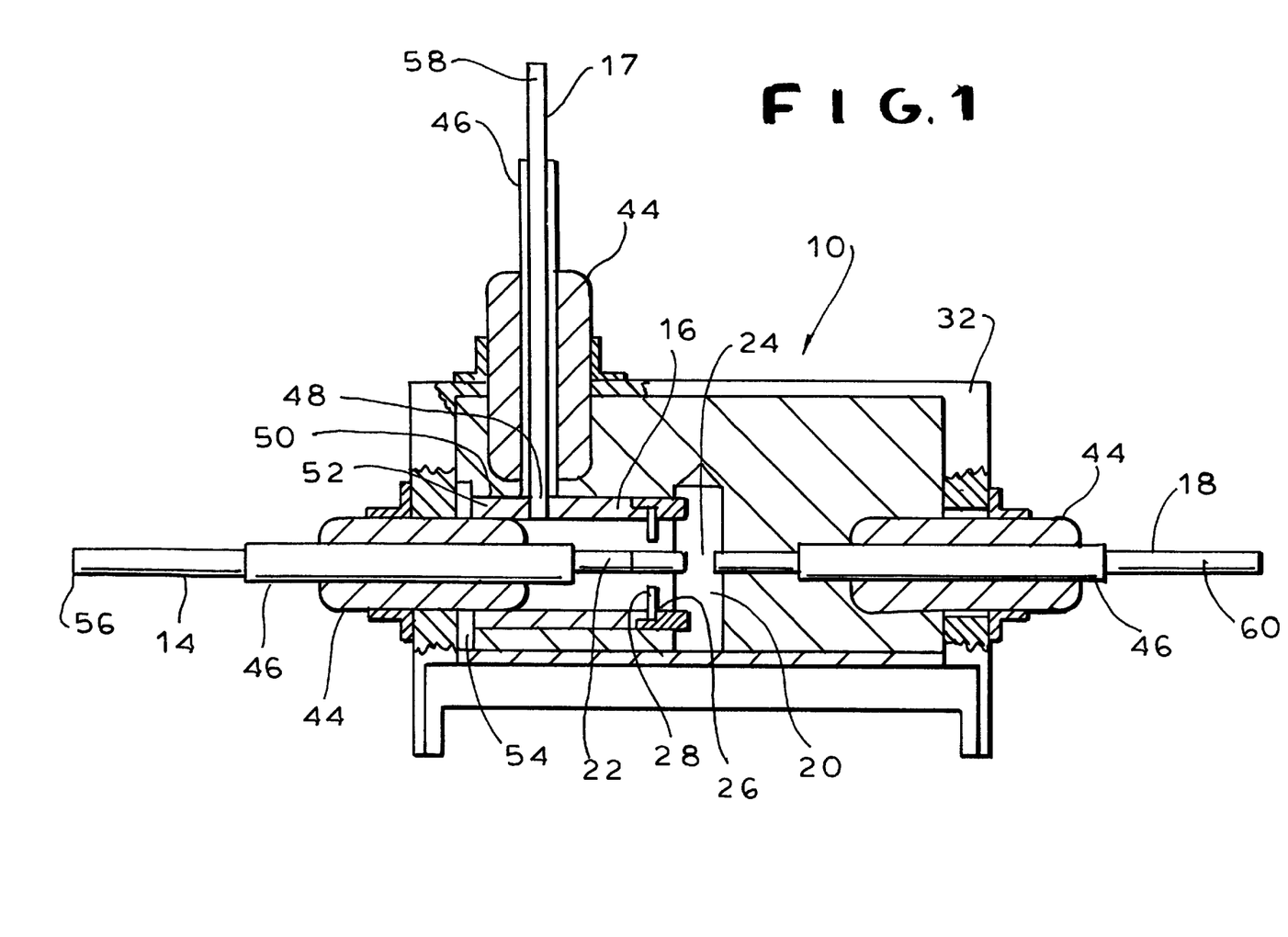
FIG. 1 is a cross-sectional side view of the body of an MVID made in accordance with the present invention.
Figure 2:
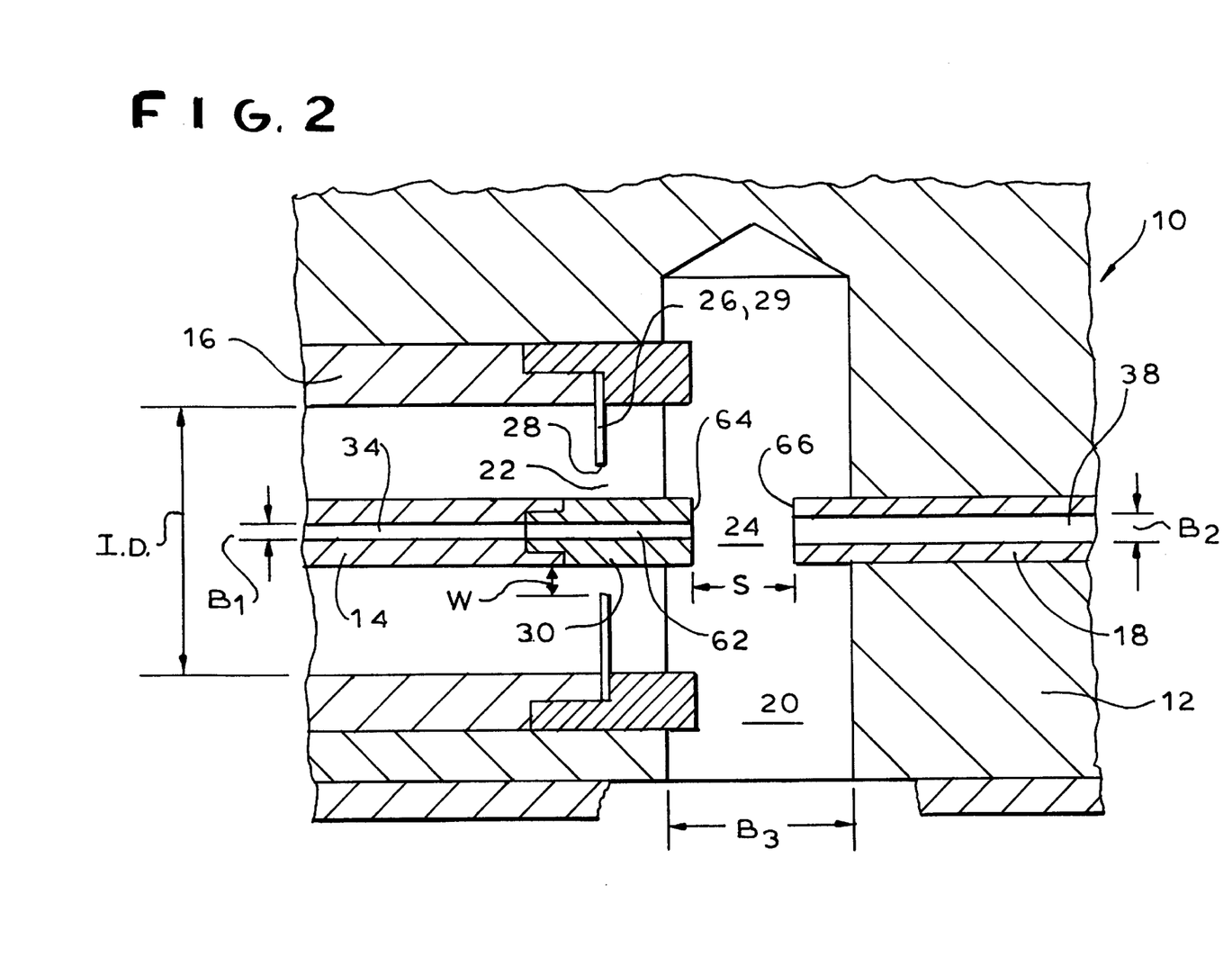
FIG. 2 is an enlarged cross-sectional side view of the MVID as shown in FIG. 1.

Referring to FIGS. 1 and 2, a preferred embodiment of a microvolume ionization detector (MVID) 10 made in accordance with the invention includes an insulating body 12, an inner electrode tube 14, an outer electrode tube 16, a corona gas inlet tube 17, and a collector electrode 18. The inner electrode 14, which is preferably tubular in shape, carries sample gas from a separator (not shown), such as a gas chromatograph column (GC) into a center core 20. The sample gas consists of trace analytes (i.e. trace amounts of gas(es) to be detected) in a substantially pure carrier gas. The carrier gas is preferably helium but it can be any one of the rare gases (e.g., argon, neon, etc.). The outer electrode 16 is preferably cylindrical in shape and carries a corona gas (which is preferably a separate flow of the same carrier gas) past a corona discharge gap 22 and into the center core 20. The gap 22 and the inner electrode 14 are preferably aligned concentrically so the corona gas flows concentrically with the sample gas into the center core 20. The collector electrode 18 is preferably aligned coaxially with the gap 22 and the inner electrode 14 so that the gases can flow readily into the collector electrode 18 and out of the MVID 10. Thus, the three MVID electrodes 14, 16, 18 serve as gas delivery means as well as electrodes so that the corona gas and sample gas mixture can be supplied directly to the very small volume between end faces 64, 66 of the inner electrode 14 and collector electrode 18, this volume being defined as the active volume 24.

Preferably the outer electrode 16 includes a gap forming means 26 which projects radially inwardly therefrom. Preferably the inner electrode 14 is tubular in shape and the gap forming means 26 has a complementary circular opening 28 forming a narrow, substantially uniform annular gap 22 which is concentric with the inner electrode 14. If, as in the preferred embodiment, the outer electrode 16 is also tubular, the gap forming means 26 can be a disc 29. Additionally, a tip 30 of the inner electrode and the gap forming means can be formed of electrically durable material, such a molybdenum.

The inner and outer electrodes 14, 16 are connected to separate power supplies (not shown) and one electrode is maintained at a considerably higher potential than the other so that a corona discharge can be established between the two electrodes. The substantially uniform width and shape of the corona gap 22 discussed above creates a substantially uniform corona discharge between the opening 28 of the gap forming means 26 and the inner electrode 14 which improves the performance of the MVID 10. The collector tube 18 is maintained essentially at ground potential.

Figure 3:
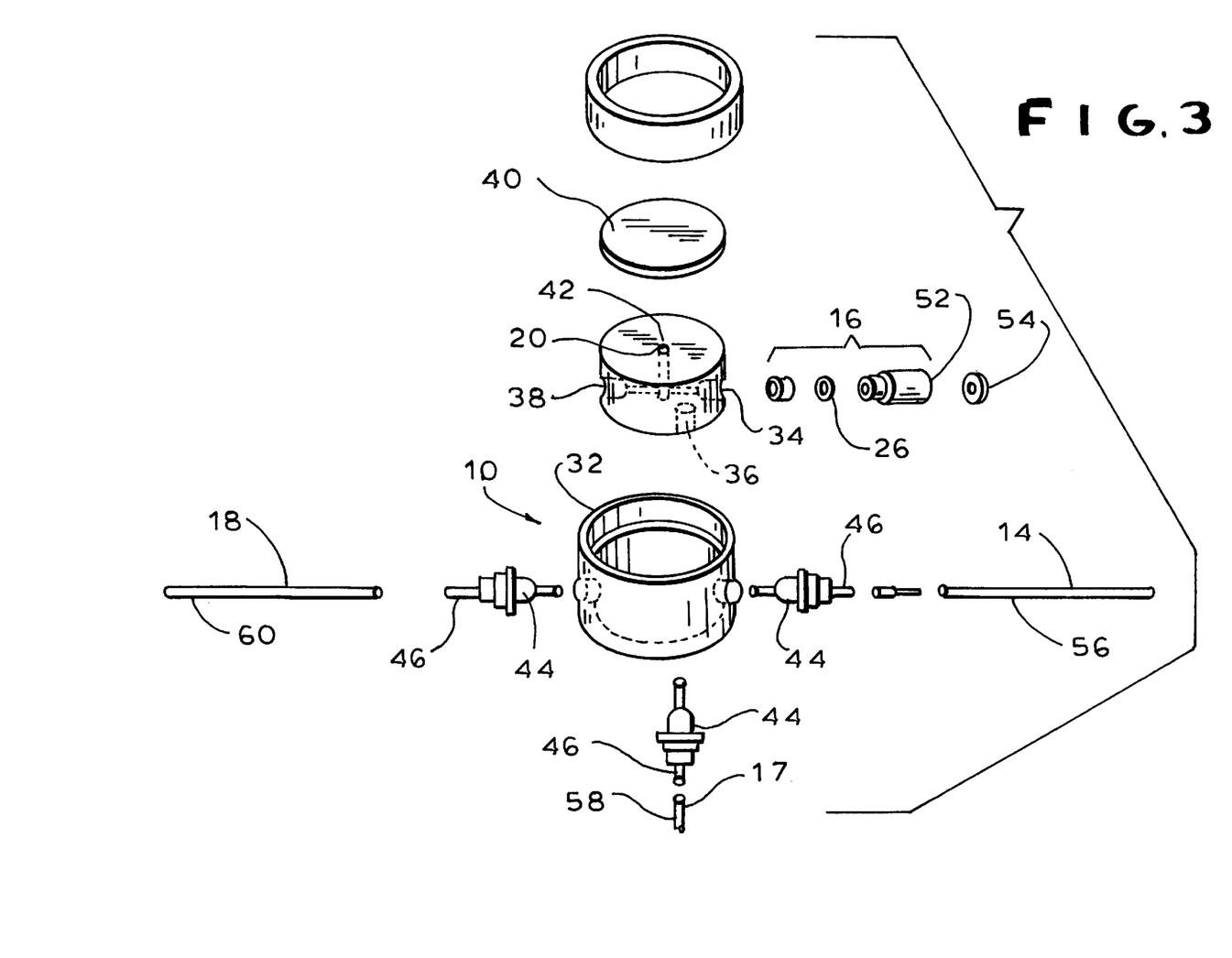
FIG. 3 is an exploded view of the MVID of FIG. 1.

Referring to FIGS. 1, 2 and 3, the body 12 of the MVID 10 is preferably made of an insulating material (such as that sold under the trademark MACOR) which can be contained in a steel case 32. The body 12 has a cavity or core 20 (which can be a cylindrical bore as shown) and three through-holes which form passageways creating a sample gas inlet 34, a corona gas inlet 36 and a gas outlet 38 leading from the exterior of the body 12 into the cavity 20. The MVID 10 can also include a cover 40, preferably also made of an insulating material, which hermetically seals an opening 42 of the above mentioned cylindrical bore.

Insulated tube feedthroughs 44 can fit within the passageways and can be hermetically sealed to the body 12. The tube feedthroughs can be soldered to the case 32 and can include metal tubes 46 to which the electrode tubes can be soldered for support. Thus, the tube feedthroughs provide electrically insulated and hermetically sealed support for the inner electrode tube 14, the corona gas inlet tube 17 and the collector electrode tube 18, all of which can extend through the case and into the body.

As shown, the inner electrode tube 14 and the collector electrode tube 18 preferably extend from the exterior of the body into the center core 20. As best seen in FIG. 1, the corona gas inlet tube 17 preferably extends from the exterior of the body 12 to a hole 48 in a wall 50 of the outer electrode the 18, which, in turn, extends into the center core 20. The tube feedthrough 44 for the sample gas inlet 34 can extend into the outer electrode tube 16 to seal a closed end 52 thereof. Additionally, an insulated spacer 54 can be disposed around the sample gas tube feedthrough 44 adjacent to the closed end 52 of the outer electrode 16 to further seal and insulate the outer electrode 16.

All of the tubes are electrically conductive so that the two independent power supplies (not shown) and the collector (not shown) can be connected to portions of the tubes outside the body 12. Specifically, one power supply can be connected to an external portion 56 of the inner electrode tube 14, the other power supply can be connected to an external portion 58 of the corona gas inlet tube 17 (which is preferably electrically connected to the outer electrode tube) and a collector (not shown), such as an electrometer, can be connected to an external portion 60 of the collector electrode tube 18. In this manner, the structure of the MVID 10 can be simplified, and separate holes through the body 12 for electrical leads can be avoided.

Referring again to FIG. 2, in the preferred embodiment, a bore $B_1$ of the inner electrode 14 is preferably about 0.3 mm and an inner diameter I.D. of the outer electrode tube is preferably about 4.4 mm. The width W of the annular gap 22 between the disk 29 and the tip 30 of the inner electrode 14 is preferably about 0.5 mm. The spacing S between the end faces 64, 66 of the inner electrode 14 and the collector electrode 18 is preferably about 1.6 mm. The electrometer electrode 18 preferably has a bore $B_2$ of about 0.7 mm and is somewhat larger than the bore of the inner electrode 14 to accommodate the sum of the gas flows from both the inner and outer electrodes 14, 16. The cylindrical bore $B_3$ in the body 12 preferably has a diameter of about 3.0 mm and is preferably about 9.0 mm deep.

The space between the inner electrode 14 and the collector electrode 18 is the active volume 24 of the MVID 10 and is well under 1 microliter. The volume of the entire center core 20 of the MVID 10 is preferably only about 40 to 60 microliters. Due to the configuration and dimensions of the MVID 10, virtually all of the gas flow from the inner electrode 14 is entrained in the outer electrode 16 flow and is carried out the collector electrode 18 gas exit.

In the operation of the MVID 10, the discharge across the corona gap 22 creates metastable species of the corona gas which interact with and ionize the analyte gas(es) in the sample gas. As the sample gas and the metastable species mix within the small active volume 24, ions of the analyte gas(es) are created which pass through the active volume 24 and into the collector electrode tube 18 wherein they are detected by the collector (not shown). The novel concentric configuration of the inner electrode 14 and the corona gap 22 creates a concentric gas flow which carries the metastable species into the center core 20 of the MVID 10 and toward the collector electrode 18. The object of the design of the MVID 10 structure is to have the neutral metastables entrain and interact with the molecules of the analyte gas in the flowing sample gas stream in the small active volume 24 between the end face 64 of the inner electrode 14 and the end face 66 of the collector electrode 18.

When operating, a high concentration of metastables should exist streaming from the corona discharge into the MVID 10 active volume 24 in a concentric fashion around the sample-gas/carrier-gas mixture. The concentric design of MVID electrodes increases the probability of the desired interactions of the metastables and analyte molecules within this small region. The coaxial alignment of the collector electrode 18 increases the probability that the ions created by the above interactions will in fact be detected by the collector. Additionally, the micro-dimensions of the MVID cavity and components allows such ionization and detection to occur with low flow rates, low concentrations and low quantities of analyte and corona gases.

In contrast to standard MID designs, no radioactive source is included in the MVID 10. The gap 22 is operated at a sufficiently high potential difference to carry a self-sustaining corona discharge and is operated under saturation conditions rather than the multiplication mode used in the triaxial detector referred to above. Under normal operating conditions, the collector measures the positive ion current produced in the gap as electrons return to the positive potential electrode. The current in the discharge may generate more metastables than may be obtained in a conventional detector. For example, at voltages ranging from +500 V to +1000 V applied to the outer electrode 16, and leaving the inner electrode 14 at ground potential, corona discharge currents between 3 and 16 microamps can be induced. With such voltages, the collector current can be two to three orders of magnitude less, ranging between $-0.8 \times 10^{-8}$ amperes to $+8.4 \times 10^{-8}$.

Figure 4:
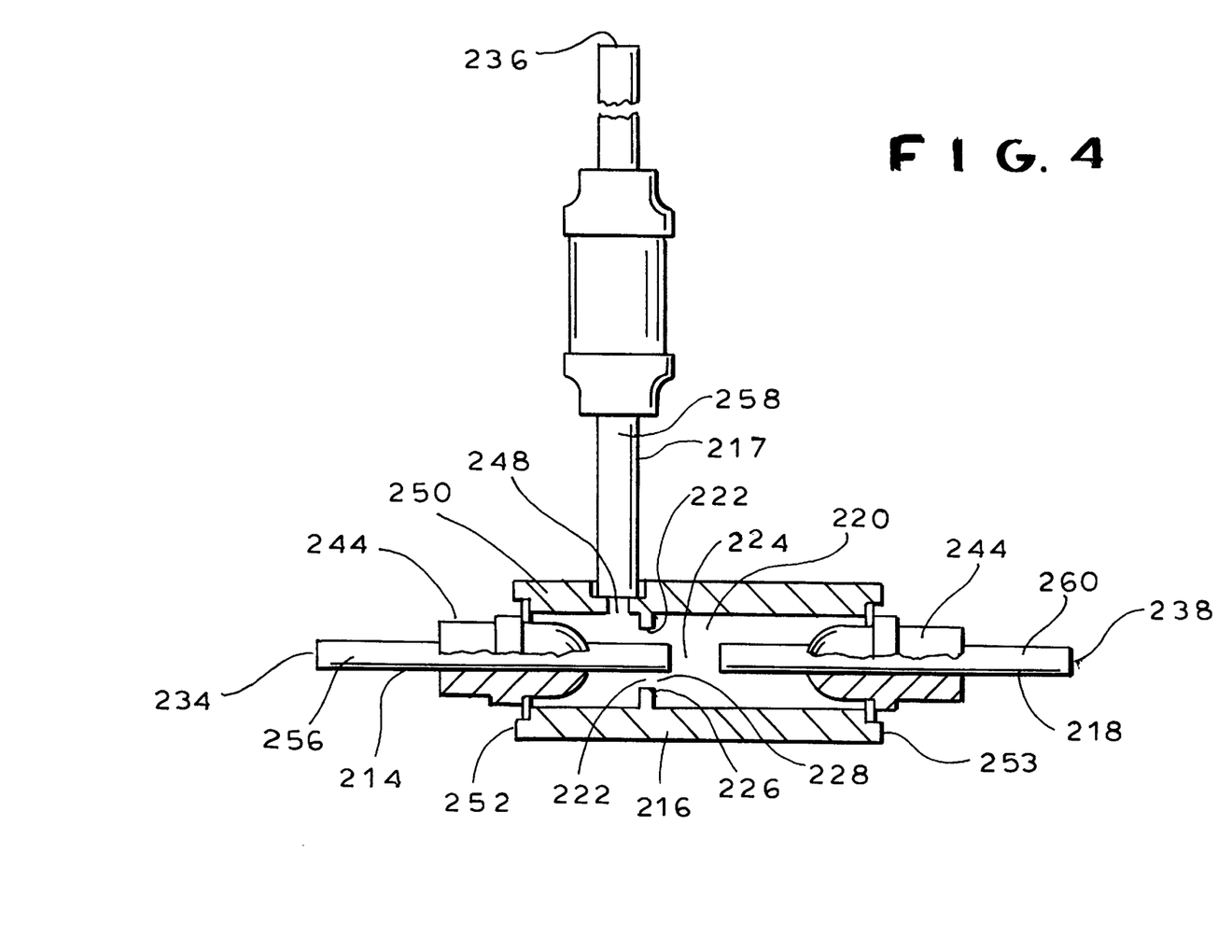
FIG. 4 is a cross-sectional side view of a second embodiment of an MVID made in accordance with the present invention.

FIG. 4 shows an alternative embodiment of the present invention having a outer electrode tube 216 disposed around and aligned concentrically with both an inner electrode tube 214 and a collector electrode tube 218 such that the center core 220 of the MVID 210 lies within a center portion of the outer electrode 216. As above, the inner electrode tube 214 is aligned coaxially with the collector electrode tube 218 and the end faces 264, 266 of the inner electrode tube 214 and the collector electrode tube 218 are spaced a short distance apart forming a small active volume 224. The outer electrode tube 218 includes a gap forming means 226 with an annular 228 opening forming a substantially uniform annular corona gap 222 concentric with the end 264 of the inner electrode 214. If the outer electrode 216 is in the form of a cylinder as shown, this gap forming means 226 can be an annular disc.

Preferably the inner electrode 214 is a hollow tube forming a sample gas inlet 234 into the cavity 220. Preferably the collector electrode 218 is also a hollow tube forming a gas outlet 238 allowing gas to exit the cavity. Also, preferably a corona gas inlet tube 217 is in fluid communication with the outer electrode 216 through a hole 248 in a wall 250 thereof forming a corona gas inlet 236 for delivery of corona gas into the center core 220 through the corona gap 222. The inner electrode tube 214 can be hermetically sealed to a first end 252 of the outer electrode 218 while the collector electrode tube 218 is hermetically sealed to a second end 253 of the outer electrode 218. The corona gas inlet tube 217 is hermetically sealed to the hole 248 in the wall 250 of the outer electrode tube 216 between the first end 252 and the gap forming means 226.

The inner electrode tube 214 and collector electrode tube 218 are electrically insulated from the outer electrode 216 by insulators 244 which are preferably ceramic seals, such as Ceramaseal Terminals, TIG welded to the outer electrode 218 as shown. Preferably the corona gas inlet tube 217 is electrically connected to the outer electrode tube 216 (such as with a TIG weld), and preferably the inner electrode tube 214 and the collector electrode tube 218 extend out of the cavity 220 so that all necessary electrical leads (not shown) need not extend into the MVID cavity 220. Specifically, preferably a first power source (not shown) is connected to an external portion 256 of the inner electrode 214, a second power source (not shown) is connected to an external portion 258 of the corona gas inlet tube 217, and the collector (not shown) is connected to an external portion 260 of the collector electrode tube 218.

As previously described, the first and second power sources create a corona discharge forming metastable species of the corona gas passing through the corona gap 222. The metastable species flow concentrically with the sample gas flowing from the inner electrode 214 into the small active volume 224 wherein the metastable species interact with and ionize the analyte gases in the sample gas mixture. The gases flow across the active volume 224 into the collector electrode tube 218 wherein the ionized analytes are detected by the collector. As will be discussed in detail below, preferably the MVID 210 is connected to a gas analysis system which provides purification of the corona and carrier gases and which provides separation of the various analytes in the sample gas mixture so that the particular analytes can be positively identified by their arrival time at the electrometer electrode 218.

Figure 5:
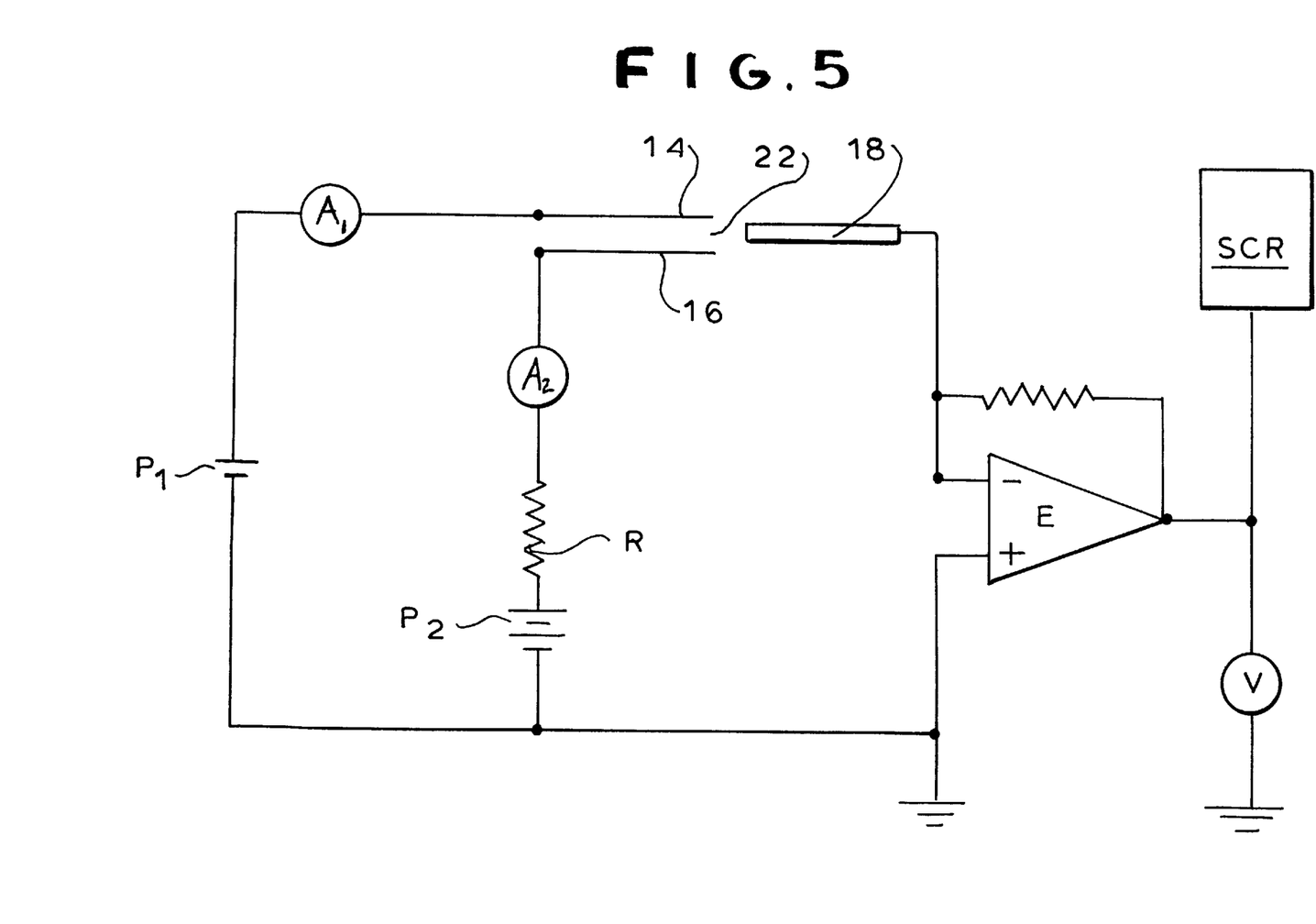
FIG. 5 is a schematic of the electrical circuitry of the MVID of FIG. 1.

FIG. 5 shows a schematic of the basic electrical operation and readout circuit used for the MVID 10. The inner and outer electrodes 14, 16 are individually connected to separate power supplies $P_1$, $P_2$, as shown. Preferably, the power supply $P_2$ connected to the outer electrode 16 is of a higher voltage than the power supply $P_1$ that connected to the inner electrode 14. In this manner, both the inner and outer electrodes 14, 16 can be maintained at a higher potential than the collector electrode 18 while inducing a corona discharge between the inner and outer electrodes 14, 16. Preferably the current directed through the outer electrode 16 to the corona discharge is limited by a resistor R, such as a 20 megohm or 250 megohm resistor, in series with the higher voltage power supply $P_2$. Current passing through the corona discharge against the lower voltage power supply $P_1$ can be measured using an ammeter $A_2$. The current coming from the high voltage supply $P_2$ can be measured using a second ammeter $A_2$, as shown, which can serve to indicate if breakdown is occurring other than in the corona.

It has been found that the corona discharge is initiated whenever the voltage across the gap exceeds 600 volts and the corona current falls to zero when the corona voltage is reduced below 380 volts. Therefore, the voltage across the gap 22 can be initiated at or above about 600 volts and maintained at or above about 380 volts. Additionally, the voltage can be maintained at a fixed level to maintain a steady DC corona discharge or it can be oscillated to generate a pulsed corona discharge if desired.

The collector, which is preferably an electrometer, is generally referred to as E, and is connected to the electrometer electrode 18. Also, one or more read out devices, such as a strip chart recorder SCR and/or a voltmeter V, can be connected to the electrometer E. The higher voltage supply $P_2$, typically operated between +400 V and +1200 V, can be a Fluke 408B high voltage power supply. The lower voltage supply $P_1$, typically operated between −40 V and +50 V, can be a Hewlett-Packard Model 6525A DC power supply.

When, as mentioned above, the inner and outer electrodes 14, 16 are operated at sufficient voltages, an electric current is produced in the gap 22 between the inner and outer electrodes 14, 16. Additionally, neutral metastable helium atoms are produced in the gap 22. These energetic neutral atoms diffuse into the gap between electrodes 14, 16 and are able to efficiently ionize non-helium sample atoms that enter said gap. The sample ions formed in this manner generate a current in the collector electrode 18 and electrometer circuit. After amplification, the electrometer circuitry outputs the signal as a voltage which can be measured using the voltmeter V or strip chart recorder SCR. For example, with a $10^8$ ohm resistance in the electrometer circuitry (as shown), an ion current of $10^{-8}$ amperes into the electrometer reads out as one volt.

Figure 6:
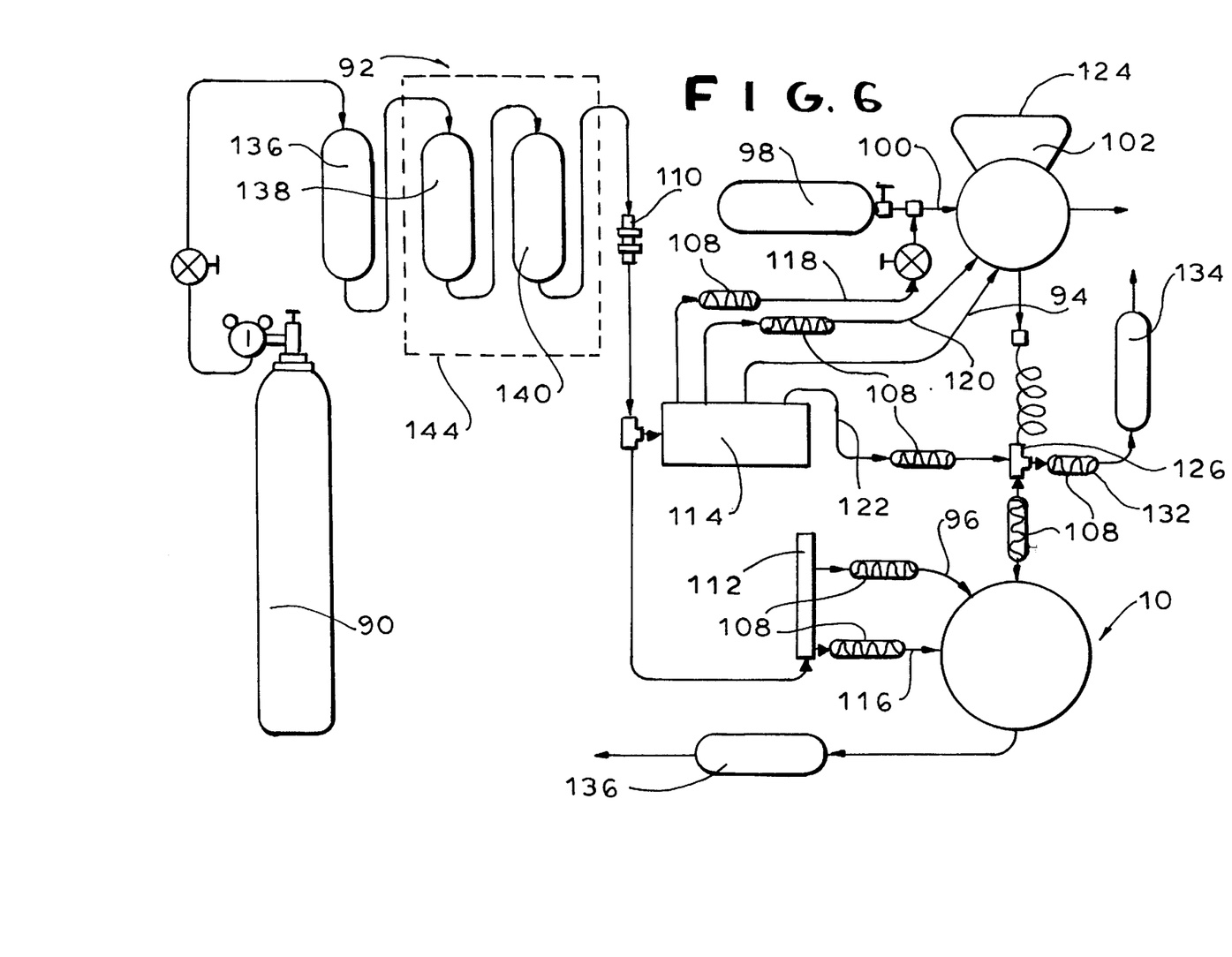
FIG. 6 is a schematic diagram of a gas analysis system incorporating an MVID of the present invention.

FIG. 6 shows a schematic of a basic flow of a gas analysis system incorporating an MVID 10 made in accordance with the present invention. Generally, a high pressure source 90 of a purified rare gas (such as helium) is directed through a purification system generally referred to as 92 and fed into the MVID 10 as both a carrier gas 94 and a corona gas 96. As will be further described below, the gas source 90 can also be used to purge various components of the system. A source 98 of sample gas 100 is mixed with the carrier gas 94 in a sample valve 102 and is directed through a separator 104, such as a GC column. The sample and carrier gas mixture 106 is then introduced into the MVID 10 through the inner electrode (not shown). The corona gas 96 is introduced into the MVID 10 through the corona gas inlet (no shown) which leads into the outer electrode (not shown).

Generally, gas flow control in the system can be accomplished using flow restrictors 108 which can consist of lengths of stainless steel tubing having wire inserts to retard the gas flow. The restrictors 108 can also be flattened until the desired flow is established. In any case, preferably high pressure helium gas 90 from a purified supply 92 connects to the MVID 10 plumbing through a leak-free joint 110 such as a VCR union. The flow can then be split through separate gas flow manifolds 112, 114. One manifold 112 provides the outer electrode corona gas 96 and optional flange purge gas 116 directly to the MVID 10 through two flow restrictors as shown. Since this gas flows directly to the MVID 10, preferably all of the gas flowing along these paths is in a completely sealed and leak-free system. The second manifold 114 supplies the gas separator 104 (such as the GC column shown) and various purge flows. Three restrictors connected to the second manifold 114 provide purge gas 118, 120, 122, to the sample valve 102, a sample loop 124 and a T connection 126 to the separator 104. A fourth port in the second manifold 114 connects directly to the sample valve 102 (i.e. without a restrictor) and provides the above mentioned high pressure carrier gas flow 94 to the separator 104.

It can be noted that the connections to the second manifold 114 need not be absolutely leak-free because the purge gases do not require absolute cleanliness. The only requirement for purge gases is that they keep out most of the ambient air and humidity. Also, the carrier gas flow 94 to the separator 104 is cleaned by the column itself, which preferably does not readily elute water at room temperature. Thus, connectors such as Swagelok fittings can be used for the second manifold 114 as well as for the T connection 126 between the separator 104, a separator vent 130, and the MVID 10.

The sample valve 102 can be a Carle micro-volume, 6-port purged sample valve (Hach part no. 72301-10) equipped with three gas inlets and a 40 microliter sample loop, or one of a similar type. In the normal standby or "run" position of this type of valve 102, the gas flow passes continuously from the high pressure column supply 94 through the microliter sample loop 124. When the valve 102 is switched to the "load" position, the sample loop 124 is switched out of this flow and into the valve loop flow 120 of about 90 ml/min. In this position, the loop 124 can also be filled from the pressurized sample gas container 98. When this is done, the valve loop flow 120 is shut off so as not to dilute the sample gas 100. When the switching gas is put back in its normal "run" position, the carrier gas flow 94 flushes the contents of the sample loop 124 onto the separator 104.

The sample loop 124, and connecting lines from the sample inlet to the column are all preferably wrapped in heating tape and insulation (not shown) and are heated to about 110° C. for sample introduction. The gas flow manifolds 112, 114 and the restrictors providing the corona gas 96 and flange purge gas 116 to the MVID 10 are also preferably heated to about 110° C. by appropriate heating means. Typically the MVID unit 10 is operated at a temperature of about 100° C., while the sample valve 102 is operated at about 128° C.

The separator 104 can be a packed Gas Chromatograph column such as is described as 1/16 inch by 5 inch s.s.

2,6-dichlorophenylisocyanate on 100/150 Porasil C, the performance characteristics of which are generally known. Briefly, this column provides rapid and effective separations for many volatile non-polar compounds, such as low molecular weight alkanes, fixed gases, and Freons. This type of column, which is preferably run at ambient temperature, has the virtue of retaining water so that the MVID detector 10 can be kept relatively dry even though gas samples with possibly relatively high moisture levels are injected. Alternatively, a microbore column can be used in place of a GC column.

Preferably, if a GC column is used, it is baked out at approximately 100° C. for cleanup and to remove any retained water prior to use. The column can be wrapped with a separately controlled heating tape with insulation (not shown) for use during bake out. Normally this would not be used during operation of the MVID since the column is operated at ambient temperatures (approximately 25° C.).

The optimum flow rate of gas from the separator 104 to the MVID 10 is about 4 microliters per second. Although there are commercial GC columns available with inner diameters of 0.05 mm which may provide such a flow rate, other types of GC columns, such as of the type described above, produce a flow rate of about 10 to 20 ml per minute. With such a GC column, the helium flow rate at a head pressure of 60 psig can be about 19 ml/min. Since this flow rate may be greater than desired, the column exit can be split between the MVID 10 and a vent tube restrictor 132 by the above mentioned T connection 126. Preferably, a small molecular sieve canister 134 is attached to the exit of the vent tube restrictor 132 to prevent back-diffusion of ambient air. Such a configuration can result in a GC flow rate to the MVID 10 of about 8 microliters per second, which is in the microbore column flow range. If desired, this vent tube 132 can be plugged. Also, preferably a second small molecular sieve canister 136 is attached to the gas exit of the MVID 10 to prevent back-diffusion of ambient air into the MVID 10.

Ultra pure gas is required for proper operation of the MVID. A classical method of physical and chemical adsorption on a cold surface is described below. Alternative methods using chemical reactions to purify noble gases are also available, as for example, rare earth getters available from several commercial suppliers such as SAES Pure Gas, Inc. and Ultra Pure Gas, Inc.

Other technology well-known in the art, such as the use of all metallic plumbing, which can e baked, is applicable in this instance to obtain the purest noble gas supply.

The gas purification system 92 mentioned above can include three canisters 136, 138, 140 approximately 13 inches long by 2 inches in diameter which are filled with an adsorbent material. Two of these canisters 136, 138 are filled with 13× molecular sieve and one canister 140 is filled half with 13× molecular sieve and half with activated charcoal. One-quarter inch stainless steel tubing can be brazed to the canisters and VCR-pipe fittings 142 and unions (not shown) can connect the canisters in series to a two stage pressure-reducing regulator (not shown) and to the MVID gas supply manifolds 112, 114.

Two of the canisters, 138, 140 are preferably submerged in a styrofoam insulated metal tub generally referred to as 144 which is filled with a refrigerant, such as isopropanol. A cold probe (not shown) such as a Cryocool brand immersion cooler (model CC-100-II manufactured by Neslab Instruments, Inc., Newington, N.H.) can be used to cool the refrigerant to −78° C. At these temperatures, the 13X molecular sieve can adsorb water and virtually all organics from the helium gas, down to ppb levels. With this type of purification system, standard grade tank helium can be used with the MVID 10, even though fixed gases such as oxygen and nitrogen may not removed. Also, even though extreme efforts are taken to clean up the helium gas used in the MVID, low concentrations of containment chemicals will still be present. The goal is to keep these at low ppb levels or lower.

The normal irreducible trace background chemicals in the helium gas, such as oxygen, water, nitrogen, carbon dioxide, etc., are ionized in the discharge and, probably to a greater extent, in the electrode gap 22 from the metastable helium atoms. Depending upon the concentration of these trace species, the metastable helium population may be somewhat attenuated and a measurable electrometer current will be carried by these positive ions in the normal operation of the MVID 10. While this background current, in the absence of added sample chemicals, is only a small fraction of the corona discharge current, it is preferable to keep the background impurities at the lowest level possible because these impurities may interact with the sample chemicals in a secondary reaction and suppress their detection. It is desired that the sample chemicals be ionized by a primary metastable reactant such as He and further that these ions survive to be collected at the collector (e.g. an electrometer electrode or a mass spectrometer). In the close geometries and relatively high fields of the MVID 10, ion lifetimes are short so that, in relatively pure helium, these requirements are usually met.

Figure 7:
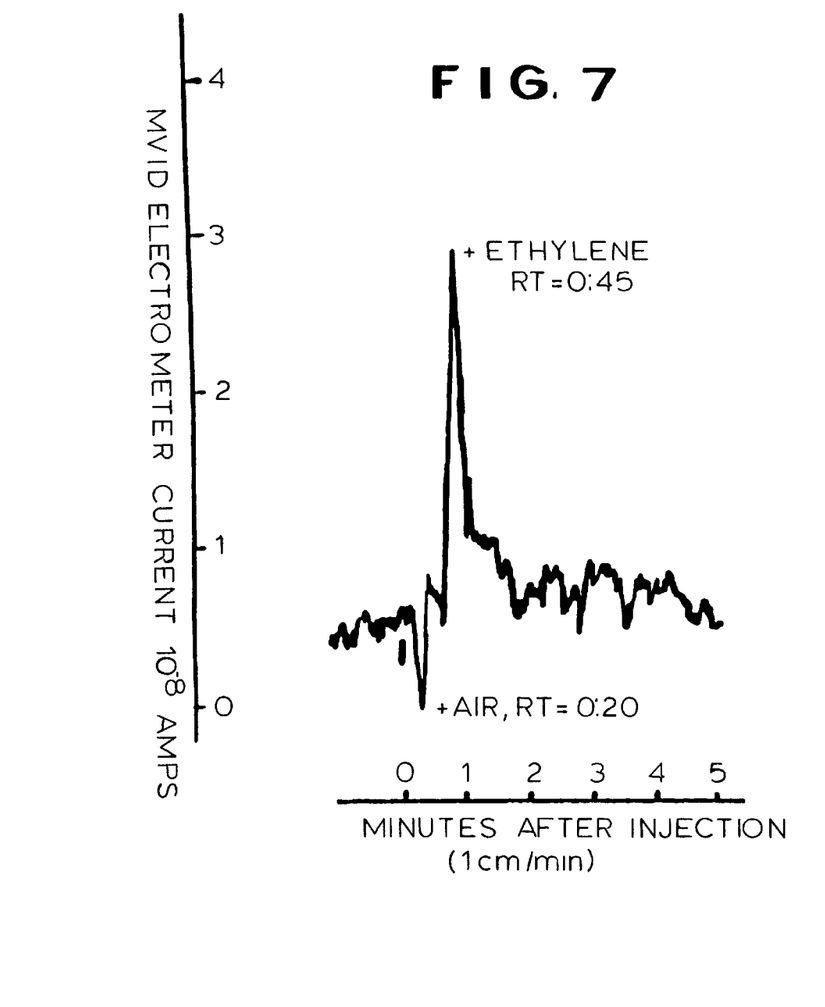
FIGS. 7 and 8 are chromatograms of tests performed with a gas analysis system incorporating an MVID made in accordance with the invention.

Referring to FIG. 7, a chromatogram produced from the injection of 1000 ppm of ethylene into the MVID 10 indicates that the MVID 10 detected the presence of ethylene after a retention time (RT) of approximately 45 seconds. For this test, the full-scale sensitivity of the electrometer was set to $5 \times 10^{-8}$ amps and the baseline electrometer current was approximately $5 \times 10^{-9}$ amps. As can be seen, the electrometer signal is somewhat noisy. However, after a retention time (RT) of 45 seconds the ethylene did produce a large tailing peak as can be seen in the figure. The amplitude of the peak was approximately $2.5 \times 10^{-8}$ amps. For this test, the GC vent 130 was plugged so that all of the GC effluent carrying the sample went into the MVID 10. Therefore the quantity of ethylene injected represented quite a large relative amount. The tailing seen in the chromatogram is probably due to the room temperature connecting pipes, which could cause some adsorption of the ethylene. The negative peak ahead of the ethylene peak has been called the "air" peak in previous work. This may represent a small quantity of ambient air from the sample valve 102, or possibly the sample cylinder 98, which passes rapidly through the separator column 104.

In this experiment, P1 was set at −20 volts, P2 was set to +430 volts, and resistor R was 20 megohms, thereby setting the inner and outer electrodes 14, 16 to −20 volts and +274 volts, respectively, and generating a corona current of $7.8 \times 10^{-6}$ amps. The GC vent tube 130 was plugged while the MVID 10 was maintained at 100 degrees Celsius and other components were at room temperature. The helium pressure was 50 psi.

Figure 8:
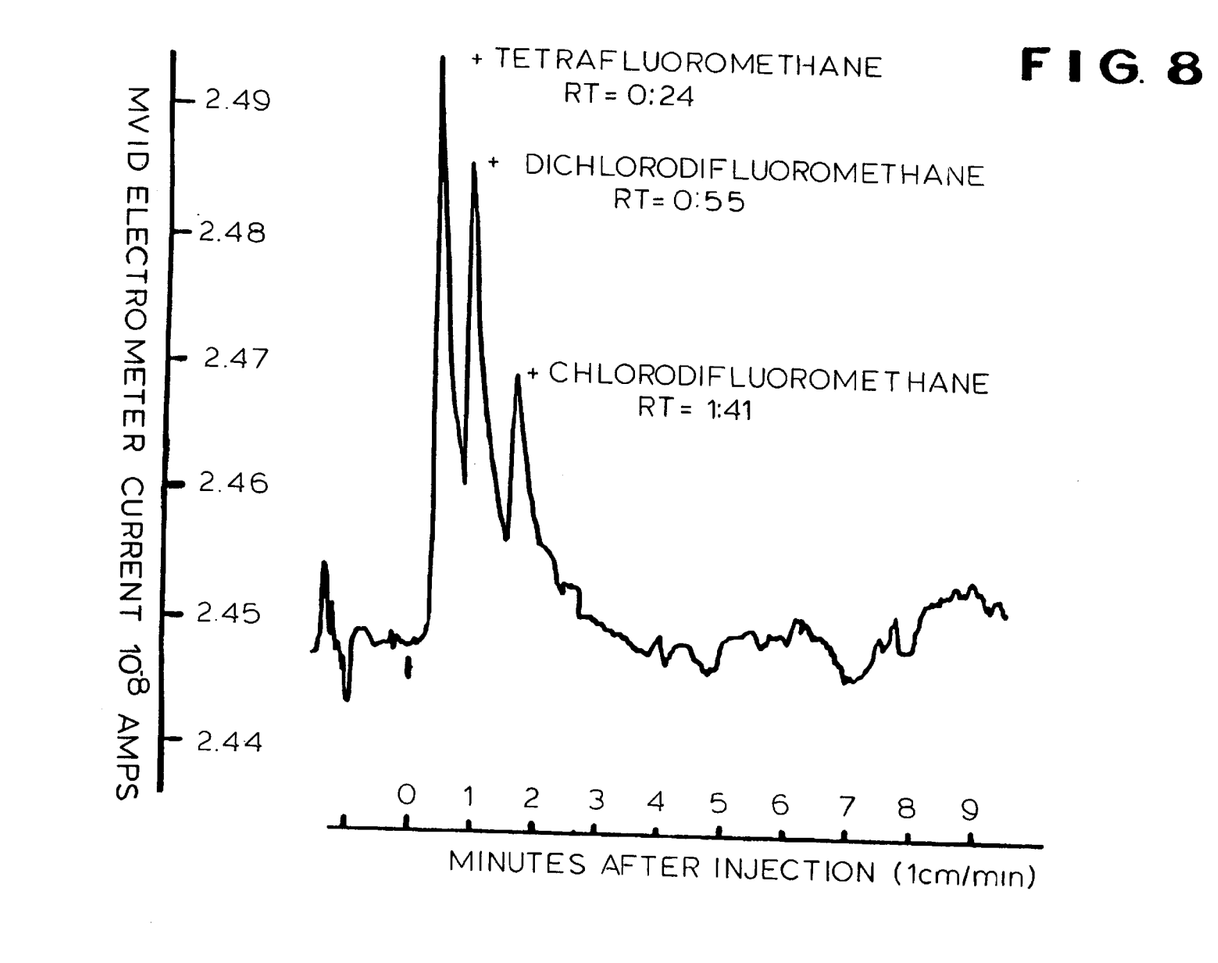

Referring to FIG. 8, a mixture of four Freons in helium analyzed with a system incorporating the MVID 10 of the present invention is shown in a chromatogram. The pressurized gas mixture contained the following components in helium:

| | | |
|---|---|---|
| Dichlorodifluoromethane | ($CCl_2F_2$) | 2.85 ppm |
| Chlorodifluoromethane | ($CHClF_2$) | 5.17 ppm |
| Tetrafluoromethane | ($CF_4$) | 5.74 ppm |
| Hexafluoromethane | ($C_2F_6$) | 8.80 ppm |

Three of the four Freons were detected as indicated on the figure. Full-scale sensitivity was only $6.25 \times 10^{-10}$ amps. Even though these chemicals were at about 17 to 35 times less concentration than the ethylene hydrocarbon previously injected, strong peak signals were produced. As can be seen from the figure, the MVID 10 detected the presence of Tetrafluoromethane, Dichlorodifluoromethane and Chlorodifluoromethane after approximately 24 seconds, 55 seconds, and 1 minute and 41 seconds, respectively.

For this experiment P1 was set at −40 volts, P2 was set at +1200 volts and resistor R was 250 megohms. This resulted in the inner and outer electrodes 14, 16 being maintained at −40 volts and +282 volts, respectively, generating a corona current of $3.67 \times 10^{-6}$ amps. The MVID 10 was maintained at 100 degrees Celsius while the gas lines and the sample valve 102 where heated to 110 and 128 degrees Celsius, respectively. The GC vent tube 130 was open and the helium pressure was 60 psi. The quantities of the different chemicals injected into the MVID 10 in the above described experiments are calculated and represented in Table 1.

QUANTITIES OF SAMPLE CHEMICALS
INTRODUCED INTO THE MVID

| Sample Chemical | Concentration (ppm) | Restrictor | GC Vent Sample Quantity |
|---|---|---|---|
| Ethylene | 1000 | closed | 34 ng |
| Tetrafluoromethane | 5.74 | open | 80 pg |
| Dichlorodifluoromethane | 2.85 | open | 55 pg |
| Chlorodifluoromethane | 5.17 | open | 71 pg |

The effect of opening or closing the GC vent line 130 is accounted for in the table and, as can be seen, the levels injected range from 34 ng for the initial high concentration ethylene injection to tens of picograms for the Freons which were most sensitively detected.

It should be understood, of course, that the specific form of the invention herein illustrated and described is intended to be representative only, as certain changes may be made therein without departing from the clear teachings of the disclosure. Specifically, the collector described above can be any type of ion detector, such as a mass spectrometer or ion mobility spectrometer, or an electrometer. Accordingly, reference should be made to the following appended claims in determining the full scope of the invention.

We claim:

1. A microliter-sized metastable ionization device for the detection of trace analytes mixed with a carrier gas, which comprises:

a cavity, a sample gas inlet, a corona gas inlet and a gas outlet;

a first electrode having a hollow end disposed in said cavity, said hollow end being in fluid communication with said sample gas inlet for pressurized delivery of a mixture of analytes and carrier gas into said cavity;

a second electrode disposed around said first electrode adjacent said hollow end thereof, a means to form a corona gap between said first and second electrodes;

said second electrode being in fluid communication with said corona gas inlet for delivery of a corona gas through said corona gap and into said cavity;

a collector having a hollow end portion in fluid communication with said gas outlet for the outgassing of gases delivered through said first and second electrodes;

a first power supply connected to said first electrode; and a second power supply connected to said second electrode;

whereby trace analytes in the carrier gas may be detected by introducing the trace analytes mixed with the carrier gas under pressure through said first electrode and simultaneously introducing a corona gas under pressure through said second electrode while maintaining an electrical potential across said corona gap sufficient to sustain a corona discharge thereacross thereby creating metastable forms of the corona gas which mix with the analyte and carrier gas mixture initiating reactions whereby the analytes are ionized and then detected by said collector as the mixture exits through the gas outlet.

2. A microliter-sized metastable ionization device as in claim 1 wherein:

said hollow end portion of said first electrode further comprises an end face and is tubular in shape;

said corona gap forming means further comprises an opening disposed around and aligned substantially concentrically with said tubular end portion of said first electrode, said opening forming a narrow and substantially uniform annular corona gap between said first and second electrodes;

whereby a substantially uniform corona discharge can be generated in said gap while said corona gas passes therethrough creating metastable forms of said corona gas which flow in a concentric manner with said analyte and carrier gas mixture into said cavity wherein the analytes in the carrier gas are ionized and are then detected by said collector.

3. A microliter-sized metastable ionization device as in claim 2 wherein:

said end portion of said collector has an end face spaced from said end face of said first electrode, and has a tubular opening which is aligned substantially coaxially with said end portion of said first electrode;

whereby gases introduced into said cavity through said first electrode are substantially entrained in said corona gas introduced through said corona gap and pass into said hollow end portion of said collector whereafter analyte ions are detected.

4. A microliter-sized metastable ionization device as in claim 3 wherein:

said first electrode further comprises a hollow tubular member;

said second electrode further comprises a cylindrical member aligned concentrically with said tubular member, said cylindrical member, having an inside diameter greater than an outside diameter of said tubular member, and having a wall with a hole in fluid communication with said corona gas inlet; and said gap forming means further comprises an annular disc projecting radially inwardly from said cylindrical member forming said annular corona gap between said first and second electrodes.

5. A microliter-sized metastable ionization device as in claim 4 wherein said cylindrical member further comprises a first end hermetically sealed to said tubular member, and said corona gas inlet communicates with said hole in said cylindrical member between said first end and said corona gap such that said corona gas introduced between said first and second electrodes exits through said annular corona gap and enters said cavity.

6. A microliter-sized metastable ionization device as in claim 5 wherein:

said corona gas inlet further comprises a corona gas inlet tube hermetically sealed to said cylindrical member, said collector further comprises a collector tube, and said ionization device further comprising an insulating body;

said cylindrical member is disposed in said body;

said tubular member extends through said body and into said cavity forming said sample gas inlet, said tubular member being aligned substantially concentrically with said cylindrical member and being hermetically sealed to said first end of said cylindrical member;

said collector tube extends through said body and into said cavity forming said gas outlet, said collector tube being hermetically sealed to said body and being substantially coaxially with said tubular member; and said corona gas inlet tube extends through said body forming said corona gas inlet.

7. A microliter-sized metastable ionization device as in claim 6 wherein said tubular member, said corona inlet tube, said cylindrical member and said annular disc are comprised of electrically conductive materials, wherein said first power supply is connected to said tubular member and said second power supply is connected to said corona inlet tube, and wherein said tubular member and said collector tube are electrically insulated from one another as well as from said cylindrical member and said corona gas inlet tube.

8. A microliter-sized metastable ionization device as in claim 7 wherein said first and second power sources are connected to said tubular member and said corona gas inlet tube, respectively, at points external to said body.

9. A microliter-sized metastable ionization device as in claim 8 wherein said end portion of said first electrode and said annular disc are comprised of molybdenum.

10. A microliter-sized metastable ionization device as in claim 9 wherein said collector further comprises an electrometer tube.

11. A microliter-sized metastable ionization device as in claim 10 wherein:

said cylindrical member has an inside diameter of about 4.4 mm;

said tubular member has an outside diameter of about 1 mm and an inside diameter of about 0.3 mm;

said annular gap between said disc and said first electrode is about 0.5 mm;

said end face of said first electrode is spaced from said end face of said third electrode by about 1.6 mm;

said cavity has a volume of about 40 to 60 micro liters; and said cavity further comprises a cylindrical bore having a diameter of about 3 mm and a depth of about 9 mm; and whereby the volume of said cavity is about 60 microliter and an active volume between said end faces of said first and third electrodes is less than 1 microliter.

12. A microliter-sized metastable ionization device as in claim 5, wherein said corona gas inlet further comprises a corona gas inlet tube hermetically sealed to said hole in said cylindrical member between said first end thereof and said corona gap;

said collector further comprises a collector tube;

said tubular member extends through said first end of said cylindrical member to said corona gap thereby forming said sample gas inlet;

said collector tube extends through a second end of said cylindrical member to a point spaced from said end face of said tubular member forming said gas outlet; and said tubular member and said collector tube being hermetically sealed to said first and second ends of said cylindrical member, respectively, thereby forming said cavity within said cylindrical member having two gas inlets and a gas outlet.

13. A microliter-sized metastable ionization device as in claim 12 wherein said tubular member, said corona inlet tube, said cylindrical member and said annular disc are comprised of electrically conductive materials, wherein said first power supply is connected to said tubular member and said second power supply is connected to said corona inlet tube, and wherein said tubular member and said collector tube are electrically insulated from one another as well as from cylindrical member and said corona gas inlet tube.

14. A microliter-sized metastable ionization device as in claim 13 wherein said end portion of said first electrode and said annular disc are comprised of molybdenum.

15. A microliter-sized metastable ionization device as in claim 14 wherein said collector further comprises an electrometer circuit.

16. A microliter-sized metastable ionization device as in claim 15 wherein:

said cylindrical member has an inside diameter of about 4.4 mm;

said tubular member has an outside diameter of about 1 mm and an inside diameter of about 0.3 mm;

said annular gap between said disc and said first electrode is about 0.5 mm;

said end face of said first electrode is spaced from said end face of said collector by about 1.6 mm;

said cavity has a volume of about 40 to 60 micro liters; and an active volume between said end faces of said first and third electrodes is less than 1 microliter.

17. A microliter-sized metastable ionization device for the detection of trace analytes mixed with a carrier gas, comprising:

a center core, first and second gas inlets and a gas outlet;

a first electrode having a hollow tubular end portion in fluid communication with both said first gas inlet and said center core for delivery of the analyte and carrier gas mixture into said center core;

a second electrode having an annular gap forming means disposed around said hollow end portion of said first electrode, said gap forming means forming a substantially concentric and uniform annular gap between said first and second electrodes;

said gap being in fluid communication with, on one side, said second gas inlet and, on the other side, said center core for delivery of a corona gas through said corona gap and into said center core;

a means to generate a corona discharge across said corona gap for creating metastable forms of said corona gas as said corona gas passes through said gap;

a collector having a hollow end portion in fluid communication with both said center core and a gas outlet for the outgassing of gases within said center core, said collector being aligned to receive gases expelled from said first electrode; and means to detect ions formed in said center core.

18. A microliter-sized metastable ionization device as in claim 17, wherein said hollow end portion of said first electrode and said hollow end portion of said collector are aligned substantially coaxially thereby providing a direct path for gas to flow from said first electrode to said third electrode.

19. A microliter-sized metastable ionization device as in claim 18, wherein said means to generate a corona discharge between said first and second electrodes further comprises a first power supply connected to said first electrode, a second power supply connected to said second electrode and a resistor connected in series between said second power supply and said second electrode.

20. A microliter-sized metastable ionization device as in claim 19 wherein said gap forming means further comprises a disc with an circular opening, said disc projecting radially inwardly from said second electrode toward said tubular end portion of said first electrode forming said substantially concentric and annular corona gap between said disc and said first electrode.

21. A microliter-sized metastable ionization device as in claim 20 wherein said collector further comprises an electrometer circuit.

22. A microliter-sized metastable ionization device as in claim 21, wherein:

said hollow end portion of said first electrode has inside and outside diameters of about 0.3 and 1.0 millimeters, respectively;

said annular gap is about 0.5 millimeters;

said electrometer tube has an inside diameter of about 0.7 millimeters;

an end face of said first electrode is spaced from an end face of said electrometer tube a distance of about 1.6 millimeters;

said center core comprise a cylindrical bore having a diameter of about 3 mm and a depth of about 9 mm; and said center core has a total volume of about 40 to 60 microliters and an active volume between said end faces of said first and electrometer tube of less than 1 microliter; and whereby said detector can operate with an analyte and carrier gas mixture flow rate of less than 4 milliliters per minute with a corona gas flow rate of about 2 milliliters per minute and can detect analytes in concentrations of less than 1 parts per million and in low picogram quantities.

23. A method to detect trace analytes in a carrier gas comprising:

(a) providing a microliter-sized ionization device with:

(i) a center core, first and second gas inlets and a gas outlet;

(ii) a first electrode having a hollow tubular end portion in fluid communication with both said first gas inlet and said center core;

(iii) a second electrode having a gap forming means with an opening disposed around said hollow end portion of said first electrode, said opening having a diameter greater than an outside diameter of said hollow tubular end portion of said first electrode forming a substantially concentric and uniform annular corona gap therebetween;

(iv) said corona gap being in fluid communication with both said second gas inlet and said center core;

(v) a means to generate a corona discharge across said corona gap;

(vi) a collector having a hollow end portion in fluid communication with both said center core and a gas outlet, said collector being aligned to receive gases expelled from said first electrode; and (vii) a means connected to said collector to detect ionized forms of the analyte;

(b) introducing an analyte and carrier gas mixture into said center core through said first electrode;

(c) introducing a corona gas through said annular gap into said center core;

(d) generating a corona discharge across said corona gap thereby creating metastable forms of the corona gas which interact with and ionize the analytes; and (e) detecting ionized forms of the analyte in said collector with said detecting means.

24. The method of claim 23 wherein said means to generate a corona discharge comprises a first power supply connected to said first electrode, a second power supply connected to said second electrode and a resistor in series with said second power supply and said second electrode.

25. The method of claim 24, wherein:

(a) said first electrode further comprise a tubular member with an end face;

(b) said second electrode further comprises a cylindrical member disposed around and aligned concentrically with said first electrode;

(c) said gap forming means further comprises a disc with a circular opening disposed around said end portion of said first electrode;

(d) said collector further comprises a tabular member aligned coaxially with said first electrode; and (e) said collector having an end face spaced a short distance from said end face of said first electrode.

26. The method of claim 25 wherein said collector further comprises an electrometer electrode.

27. The method of claim 26 further comprising:

(a) maintaining the temperature of a body of said ionization device at about 100° C.;

(b) maintaining the temperatures of said inner and outer electrodes at about 110° C.; and (c) maintaining the temperatures of said inner and outer electrodes at temperatures in the range of ambient temperature to 250° C.

28. A trace analyte detection system comprising:

(a) a detector having a cavity, having first and second gas inlets and having a gas outlet;

(b) a sample valve;

(c) a source of a purified rare gas connected to both said second gas inlet and said sample valve;

(d) a source of analytes connected to said sample valve;

(e) a gas separator connected between said sample valve and said first gas inlet; and (f) wherein said detector further comprises:

(i) an inner electrode having a hollow tubular end portion in said cavity in fluid communication with said first gas inlet;

(ii) an outer electrode in fluid communication with said second gas inlet, said outer electrode having a gap forming means with an opening aligned concentrically with said end portion of said inner electrode forming a substantially uniform corona gap in fluid communication with both said second gas inlet and said cavity; and (iii) a collector having an opening in said cavity in fluid communication with said gas outlet.

29. A trace analyte detection system as in claim 28 wherein:
   (a) said inner electrode further comprise a tubular member;
   (b) said outer electrode further comprises a cylindrical member aligned substantially concentrically with said inner electrode;
   (c) said gap forming means further comprises an annular disc projecting radially inwardly from said outer electrode toward said inner electrode forming said corona gap; and
   (d) said collector is aligned substantially coaxially with said inner electrode and said corona gap.

30. A trace analyte detection system as in claim 29 further comprising a first power supply connected to said first electrode, a second power supply connected to said second electrode, and a resistor in series with said second power supply and said second electrode.

31. A trace analyte detection system as in claim 30 wherein said collector further comprises an electrometer.

32. A trace analyte detector system as in claim 31 further comprising:
   (a) means to maintain the temperature of a body of said detector at about 100° C.;
   (b) means to maintain the temperatures of said inner and outer electrodes at about 110° C.

33. A trace analyte detection system as in claim 32 wherein said hollow tubular end portion of said first electrode and said annular disc are comprised of molybdenum.

* * * * *